(12) United States Patent
Kogler

(10) Patent No.: US 10,905,369 B2
(45) Date of Patent: Feb. 2, 2021

(54) DEVICE FOR POSTUROGRAPHY

(71) Applicant: SENSE PRODUCT GMBH, Pichling bei Stainz (AT)

(72) Inventor: Thomas Kogler, Vienna (AT)

(73) Assignee: SENSE PRODUCT GMBH, Pichling Bei Stainz (AT)

(*) Notice: Subject to any disclaimer, the term of this patent is extended or adjusted under 35 U.S.C. 154(b) by 140 days.

(21) Appl. No.: 15/502,487

(22) PCT Filed: Aug. 7, 2015

(86) PCT No.: PCT/AT2015/050192
§ 371 (c)(1),
(2) Date: Feb. 7, 2017

(87) PCT Pub. No.: WO2016/019407
PCT Pub. Date: Feb. 11, 2016

(65) Prior Publication Data
US 2017/0231549 A1    Aug. 17, 2017

(30) Foreign Application Priority Data

Aug. 8, 2014    (AT) .............................. A 50554/2014

(51) Int. Cl.
*A61B 5/00*    (2006.01)
*A63B 22/00*    (2006.01)
*A63B 22/18*    (2006.01)

(52) U.S. Cl.
CPC ........ *A61B 5/4023* (2013.01); *A63B 22/0015* (2013.01); *A63B 22/18* (2013.01);
(Continued)

(58) Field of Classification Search
CPC ... A61B 5/4023; A63B 22/0015; A63B 22/18; A63B 2220/56; A63B 2225/62; A63B 2220/24; A63B 2220/40
See application file for complete search history.

(56) References Cited

U.S. PATENT DOCUMENTS 4,491,318 A * 1/1985 Francke ............. A63B 21/0004
                                                                 482/147
5,336,144 A * 8/1994 Rodden .................. A63B 22/02
                                                                 482/51
(Continued)

FOREIGN PATENT DOCUMENTS

AT          507646 B1    11/2010
AT          509939 A1 * 12/2011 ............. A63B 22/18
(Continued)

OTHER PUBLICATIONS

Machine Translation of AT 509 939 A1 Provided by EPO (Year: 2018).*
(Continued)

*Primary Examiner* — Matthew Kremer
*Assistant Examiner* — Samuel C Kim
(74) *Attorney, Agent, or Firm* — McCoy Russell LLP

(57) ABSTRACT

The invention relates to a device for posturography having a measuring platform, which comprises a standing surface for a test person having a base element on which the measuring platform is tiltably supported by means of a tilting apparatus, and having an air cushion means with which an air cushion bearing the base element is formed, wherein a damping member having a damping material is arranged between the measuring platform and the base element, by which damping member a tilting movement of the measuring platform is damped.

21 Claims, 8 Drawing Sheets

(52) U.S. Cl.
CPC ....... *A63B 2220/24* (2013.01); *A63B 2220/40* (2013.01); *A63B 2220/56* (2013.01); *A63B 2225/62* (2013.01)

(56) References Cited

U.S. PATENT DOCUMENTS

| | | | |
|---|---|---|---|
| 5,409,226 A | 4/1995 | Mesko et al. | |
| 5,694,152 A * | 12/1997 | Loop | G06F 3/0334 345/157 |
| 5,921,899 A * | 7/1999 | Rose | A63B 5/11 482/112 |
| 7,335,146 B2 * | 2/2008 | Gerstung | A63B 69/0035 482/142 |
| 7,374,517 B2 * | 5/2008 | Lockett | A63B 21/0004 297/271.5 |
| 7,686,396 B2 * | 3/2010 | Schaaf | A47C 7/14 297/313 |
| 7,775,952 B1 * | 8/2010 | Curran | A63B 22/18 482/146 |
| 9,038,482 B2 * | 5/2015 | Xia | A43D 1/022 73/862.041 |
| 2003/0040405 A1 * | 2/2003 | Watterson | A63B 22/0207 482/51 |
| 2004/0248714 A1 * | 12/2004 | Johnsen | A63B 22/18 482/142 |
| 2008/0228110 A1 | 9/2008 | Berme | |
| 2008/0312565 A1 * | 12/2008 | Celik-Butler | A61H 31/005 601/43 |
| 2011/0111935 A1 | 5/2011 | Cole et al. | |

FOREIGN PATENT DOCUMENTS

| | | |
|---|---|---|
| AT | 509939 A1 | 12/2011 |
| CA | 2663532 A1 | 3/2008 |
| CN | 201248696 Y | 6/2009 |
| EP | 0761266 A2 | 3/1997 |
| WO | 2013134873 A1 | 9/2013 |

OTHER PUBLICATIONS

"Latch." Merriam-Webster.com. 2019. Retrieved Apr. 4, 2019 from www.merriam-webster.com/dictionary/latch (Year: 2019).*
"Tilt." Merriam-Webster.com. 2019. Retrieved Apr. 4, 2019 from www.merriam-webster.com/dictionary/tilt (Year: 2019).*
ISA European Patent Office, International Search Report Issued in Application No. PCT/AT2015/050192, dated Oct. 29, 2015, WIPO, 4 pages.
International Bureau of WIPO, International Preliminary Report on Patentability Issued in Application No. PCT/AT2015/050192, dated Feb. 23, 2017, WIPO, 7 pages.
State Intellectual Property Office of the People's Republic of China, Office Action and Search Report Issued in Application No. 201580042701.4, dated Jul. 10, 2018, 13 pages. (Submitted with Partial Translation).
State Intellectual Property Office of the People's Republic of China, Office Action and Search Report Issued in Application No. 201580042701.4, dated Apr. 30, 2019, 15 pages. (Submitted with Partial Translation).

* cited by examiner

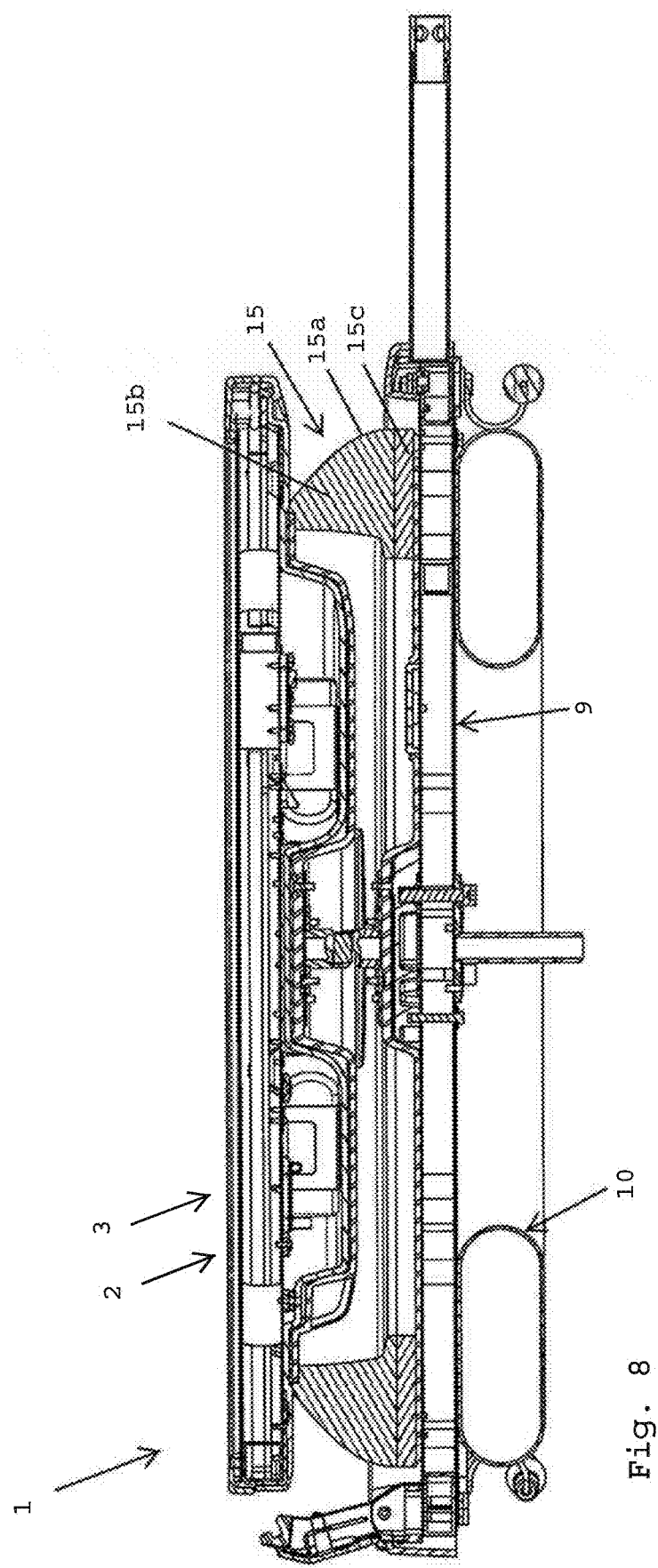

DEVICE FOR POSTUROGRAPHY

CROSS-REFERENCE TO RELATED APPLICATIONS

The present application is a U.S. National Phase of International Patent Application Serial No. PCT/AT2015/050192, entitled "DEVICE FOR POSTUROGRAPHY," filed on Aug. 7, 2015. International Patent Application Serial No. PCT/AT2015/050192 claims priority to Austrian Patent Application No. A 50554/2014, filed on Aug. 8, 2014. The entire contents of each of the above-cited applications are hereby incorporated by reference for all purposes.

TECHNICAL FIELD

The invention relates to a device for posturography having a measuring platform, which comprises a standing surface for a test person, having a base element on which the measuring platform is tiltably supported by means of a tilting apparatus, and having an air cushion means with which an air cushion bearing the base element is formed.

BACKGROUND AND SUMMARY

Such a posturography training equipment is known, for example, from AT 507 646 B1. The known balance training equipment comprises a hose ring loosely resting on a rigid base plate, which hose ring is fastened to the underside of a rigid plate. An overpressure is generated by compressed air flowing into the space delimited by the hose ring, the plate and the base plate, wherein an air cushion raising the plate is formed.

Posturography refers to methods which are used for the analysis of posture. Body sways, in particular, are registered perpendicularly at rest with posturography. It is already known in the prior art to analyze posture with force measuring plates. In this case, the position of the projection of the body's center of gravity, the so-called center of pressure can be objectively determined. If the body weight is distributed unevenly on the measuring platform, the center of pressure moves forward or backward, to the left or to the right depending on the displacement of the total body weight. Such deviations can be graphically displayed on a computer screen. These data can be used for various diagnostic purposes.

However, through extensive theoretical and practical tests, it has been shown that the known systems with force measuring plates were not able to analyze the test person's coordination and balancing abilities with the desired precision.

US 2008/0228110 A1 describes another device for posturography, which comprises a platform with a force measuring plate fastened to the upper side of a square upper plate. In addition, a square lower plate is provided, which is attached to the feet. Flexible members are arranged on the outer circumference between the upper plate and the lower plate. These members may be springs or dampers. Compressible foam material members are also given as examples. However, due to a lack of an air cushion, mobility in the horizontal direction is not available with this device, so that the test results are not satisfactory. In addition, it is disadvantageous that the spring or damping members are provided only at the corner points between the respectively square upper and lower plates. As a result, the behavior of the device is strongly dependent on the tilting direction.

WO 2013/134873 A1 describes another device in which a patient can stand on a flexible material such as foam material.

In contrast, the object of the present invention is to provide a device for posturography of the initially mentioned type with which the analysis of the posture can be improved by constructively simple means.

According to the invention, a damping member having a damping material is arranged between the measuring platform and the base element, by which damping member a tilting movement of the measuring platform is damped.

The invention is therefore based on the fact that the tilting movements of the measuring platform during the posturography are constantly cushioned or damped by the damping material so that a hard stop of the measuring platform in the vertical direction is avoided during the test. In addition, horizontal mobility of the measuring platform can be enabled with the air cushion means. The measuring platform is preferably pivotally supported about a vertical axis through the center of the measuring platform. Advantageously, therefore, mobility can especially be achieved in a particularly large number of degrees of freedom. Surprisingly, it has been found that the informative value of the measurement data can be substantially improved with the device according to the invention. The reason for this is that the test person's balance during the test program is dynamically exercised permanently, without setting to a hard end stop. The arrangement of the damping member therefore contributes significantly to the correct measurement. If, on the other hand, the measuring platform were to strike on a rigid plate, correct posturography would not be possible in one run or the measurement would be incorrect. Advantageously the results of posturography can therefore be significantly improved. The posturography apparatus according to the invention is especially suitable for developing an individual sensorimotor strength and weakness profile for the test person. In addition, effective fall prevention programs can be created. The device according to the invention advantageously combines the translational mobility of the measuring platform through the air cushion means with the damped tippability of the measuring platform through the tilting apparatus and the damping member. This results in a maximum destabilization of the test person, which enables a particularly revealing analysis.

In order to uniformly dampen the tilting movement of the measuring platform in all directions, it is advantageous if the damping material is arranged circumferentially, in particular annularly circumferentially, between the measuring platform and the base element. The damping material therefore preferably extends circumferentially with a constant cross-section between the measuring platform and the base element. Preferably, the damping material extends below a radial outer edge region of the measuring platform. In posturography, the measuring platform can be constantly tipped by the test person from the center position in any direction, wherein the subjacent section of the damping material is compressed accordingly. As a result, the tilting movement of the measuring platform can be damped to the same extent for each tilt angle. Advantageously, a hard stop of the measuring platform in the vertical direction, i.e., in the z-direction, can thus be reliably avoided, whereby the informative and prognostic power of the analysis can be substantially increased.

In order to dampen or cushion the tilting movements of the measuring platform during posturography, it is advantageous if the damping material rests in a substantially horizontal center position of the measuring platform against the underside thereof. Accordingly, the damping or cushioning action occurs immediately when the measuring platform is tipped from the substantially horizontal center position.

In order to adapt the damping characteristic, it is advantageous if the damping material is tapered in the cross-section in the direction of the measuring platform. This embodiment has the advantage that, with small deflections of the measuring platform from the center position, a weaker damping effect and thus a greater destabilization of the test person is achieved than with larger deflections of the measuring platform. Thereby the motor or coordination skills of the test person can be optimally examined.

In order to achieve the desired damping properties, both the cross-sectional geometry of the damping material as well as the damping material itself can be adapted. The more the damping material tapers towards the measuring platform, the weaker the damping effect, so that a correspondingly harder damping material should be provided. Conversely, a softer damping material may be used if the cross-sectional area of the damping material is increased.

According to a particularly preferred embodiment, the damping material comprises a substantially parabolic boundary surface in the cross-section. Thereby a progressive damping behavior is obtained, which is particularly suitable for posturography. Preferably, the outer boundary surface of the damping material as seen from the radial direction is substantially parabolic in cross-section. Advantageously, the damping effect of the damping material therefore increases continuously with increasing tilt angle. The destabilization of the test person correspondingly decreases, however without disappearing completely. The substantially parabolic boundary surface is thereby preferably formed as a bearing surface for the underside of the measuring platform.

Moreover, it is favorable if the damping material comprises a first layer on the side of the measuring platform and a second layer on the side of the base element, wherein the second layer is harder than the first layer. Accordingly, the first layer, i.e., the upper layer of the damping material relative to the operating position, is softer than the second or lower layer of the damping material. This embodiment has the consequence that the damping effect increases with the tilt angle starting from the center position of the measuring platform. Accordingly, the test person is destabilized stronger at smaller tilt angles than at larger tilt angles.

In order to avoid a hard stop for the pivoting or tilting movement of the measuring platform, it has been found to be advantageous if a foam material, in particular polyurethane, is provided as damping material. Due to the foam material, the test person remains constantly in movement on the measuring platform, whereby a particularly advantageous uninterrupted posturography is enabled. The damping material between the measuring platform and the base element is formed and arranged in such a manner that tilt angles of between 5 and 20 degrees, preferably substantially 10 degrees, each relative to the horizontal center position of the measuring platform, can be achieved in the posturography. Accordingly, the center axis of the measuring platform can be tilted from its vertical normal position in all directions by a maximum tilt angle of 5 to 20 degrees, in particular substantially 10 degrees. The tilting movement of the measuring platform is damped by the damping material until the maximum tilt angle is reached. Preferably, the maximum tilt angle is substantially 10 degrees.

In order to achieve a modular construction, it is advantageous if the damping member is connected to the base element via a releasable connection, in particular a plug connection, and/or that the measuring platform is connected to the damping member via another releasable connection, in particular another plug connection. Advantageously, the individual modules can thus be exchanged simply, in particular, without tools. This is particularly advantageous for the damping member, for which another damping material can be selected for different applications.

In order to arrange the damping member on the base element in the intended position by constructively simple means, it is advantageous if the damping member comprises at least one centering opening for receiving a corresponding centering member of the base element. Alternatively, the base element can comprise a centering opening in which a corresponding centering member of the damping member is receivable.

In order to perform the posturography optionally with and without tippings, it is favorable if at least three rocker arm members are provided between the base element or the damping member and the measuring platform, which rocker arm members can be pivoted between a release position which releases the tilting movement of the measuring platform and a blocking position which blocks the tilting movement of the measuring platform. Preferably, the rocker arm members are supported articulated on the base element. By pivoting into the blocking position, the rocker arm members are brought into abutment with the measuring platform. Alternatively, the rocker arm members can also be mounted articulated to the measuring platform. The posturography device can be used for various applications in this way. The tilting movement of the measuring platform is blocked by manual pivoting of the rocker arm members into the blocking position so that the posturography is limited to the horizontal movement, i.e., movement in the x-y-direction of the measuring platform. In order to release the pivotability of the measuring platform, the rocker arm members are pivoted into the release position.

In order to reliably maintain the rocker arm members in the blocking position, it is advantageous if latching members are provided on the rocker arm members for latching in the blocking position. Upon pivoting the rocker arm members inwards the latching connection is established. Latching lugs are preferably provided as latching members, which cooperate with corresponding latching receptacles, in particular on the measuring platform. On the one hand, thereby the measuring platform can be prevented from being inadvertently shifted between the two operating positions, with or without the possibility of tilting. On the other hand, switching is particularly simple for the user.

In order to precisely capture the weight displacements of the user on the measuring platform, it is advantageous if the measuring platform comprises a plurality of pressure sensors, which are preferably arranged substantially regularly on the standing surface. A stress profile can be created therewith. It is particularly favorable when between 4000 and 6600 sensors, preferably between 4700 and 5900 sensors, in particular approximately 5300 sensors are provided on the standing surface. Such pressure sensors are known in the prior art. The signals of the pressure sensors are transmitted to a computing apparatus for evaluation.

For posturography, it is advantageous if the measuring platform for forming the standing surface comprises a circular sensor film having the pressure sensors, which sensor film preferably is composed of multiple sensor film parts, in particular of four substantially quarter circle sensor film parts. Such sensor films having pressure sensors are known from other fields of application. For use in the device for posturography according to the invention, however, it has proved to be particularly advantageous if the circular sensor film is composed of four quarter circle shaped films which are arranged substantially gap free next to one another on the standing surface.

For processing the measurement signals, it is advantageous if the pressure sensors of the sensor film parts are connected to signal pick-ups which are connected to a computing apparatus via data transfer lines. Preferably, exactly one signal pick-up is provided per sensor film part, which signal pick-up receives the measuring signals of the pressure sensors on the respective sensor film part. The measured data are transferred via suitable data transfer lines to a computing apparatus with which an analysis of the measured data is performed.

For forming the air cushion, it is favorable if the air cushion means comprises a circumferential sealing member delimiting an overpressure chamber. The overpressure chamber is delimited by the sealing member, the base element and a sliding surface for the sealing member. As is known per se in the prior art, the overpressure chamber is connected to a compressed air apparatus via a line with which compressed air can be introduced into the overpressure chamber. Thereby an air cushion on the underside of the base element is formed, with which air cushion the horizontal mobility of the measuring platform is effected. A hose ring can be provided as a sealing member. The configuration of the air cushion means is known, for example, from AT 509 939 A1, to which reference may be made here for the sake of simplicity.

As already known from AT 509 939 A1, the base element can be arranged movably in the horizontal plane in a frame element. With regard to the support of the base element on the frame element or bottom element, reference may therefore be made again to AT 509 939 A1.

In order to avoid a hard stop for movements of the measuring platform in the horizontal plane during posturography, it is advantageous if the frame element comprises a receiving member for a guide member of the base element, wherein a damping stop is formed between the guide member and the receiving member. The damping stop comprises a damping material, for example, foam material or foam rubber, with which the stop of the guide member of the base element on the receiving member is damped. Preferably, the damping material is provided as a ring on the inside of the receiving member. Advantageously, the movements of the measuring platform can thus be performed in a damped manner in all three spatial directions.

In practice, the prior art has proven to be problematic in that the hose ring of the air cushion means is excessively deformed by weight displacements on the measuring platform. For this reason, it is advantageous if a spacer member is provided between the base element and the frame element. The spacer member is arranged to keep the distance between the sliding surface of the sealing member of the air cushion means and the base element substantially constant during posturography. Preferably, multiple spacer members are provided radially outside the sealing member in order to counteract a vertical deformation of the sealing member during loads in all directions.

In this embodiment, it is favorable if the spacer member comprises a spring member which is elastically deformable in the vertical direction. The spring members preferably each comprise at least one spring clip which is fastened to the underside of the base element.

Moreover, it is favorable if the spacer member comprises a sliding member for sliding on a sliding surface of the frame element. In particular, a ball element can be provided as a sliding member, which is located at the free end of the spring member. Preferably, each sliding member is connected to the base element via two spring clips.

BRIEF DESCRIPTION OF THE FIGURES

The invention is explained in more detail in the following with reference to a preferred exemplary embodiment, to which it is, however, not intended to be restricted. In the drawings:

FIG. 8 shows a sectional view of parts of a further device for posturography according to the invention, wherein the damping member comprises a parabolic boundary surface and a two-layered structure.

DETAILED DESCRIPTION

Figure 1:
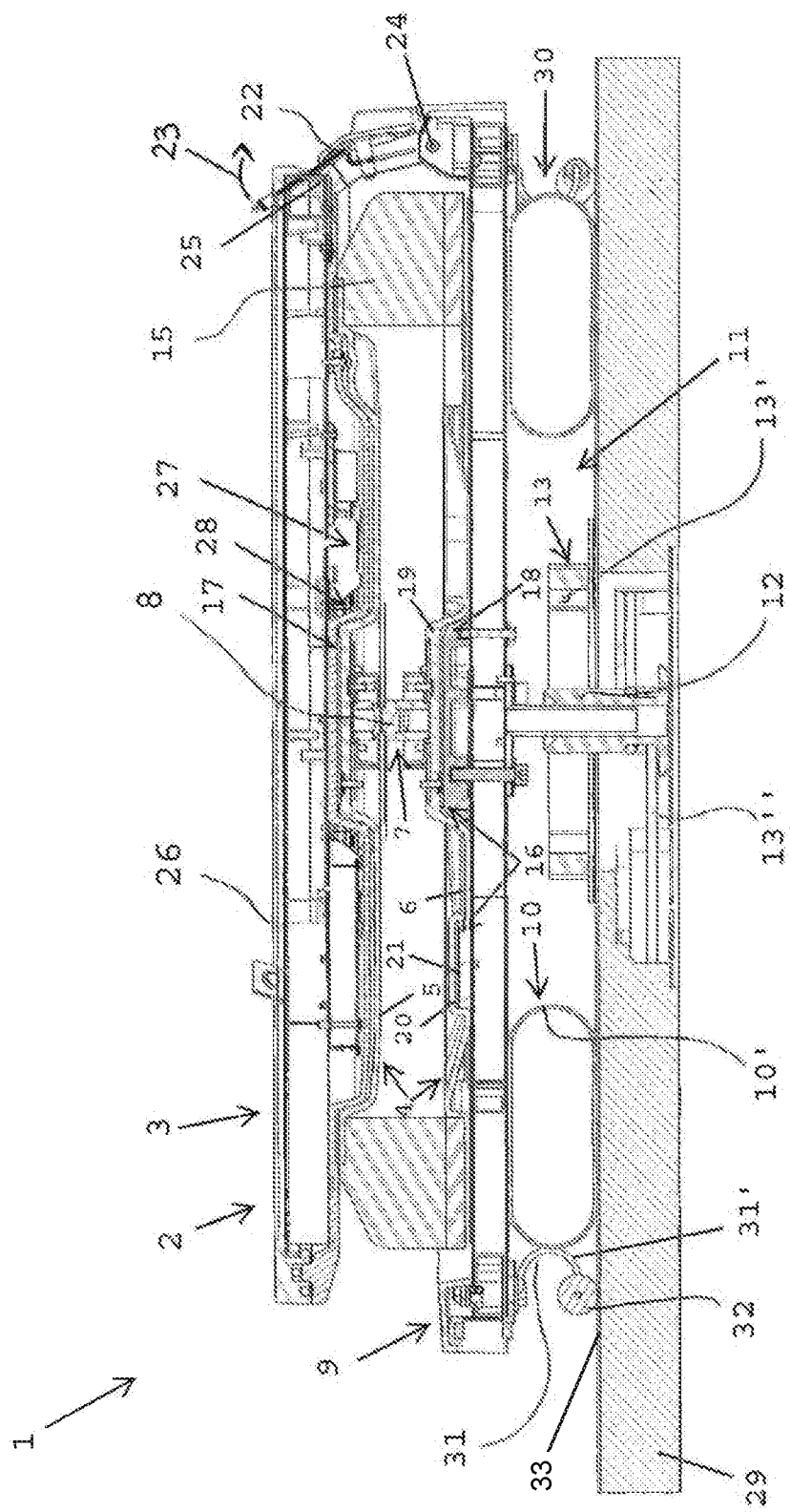
FIG. 1 shows a sectional view of a device for posturography according to the invention in modular construction with a measuring platform which is tiltably supported on a base element, wherein a damping member damping the tilting movements of the measuring platform is arranged between the measuring platform and the base element.
Figure 2:
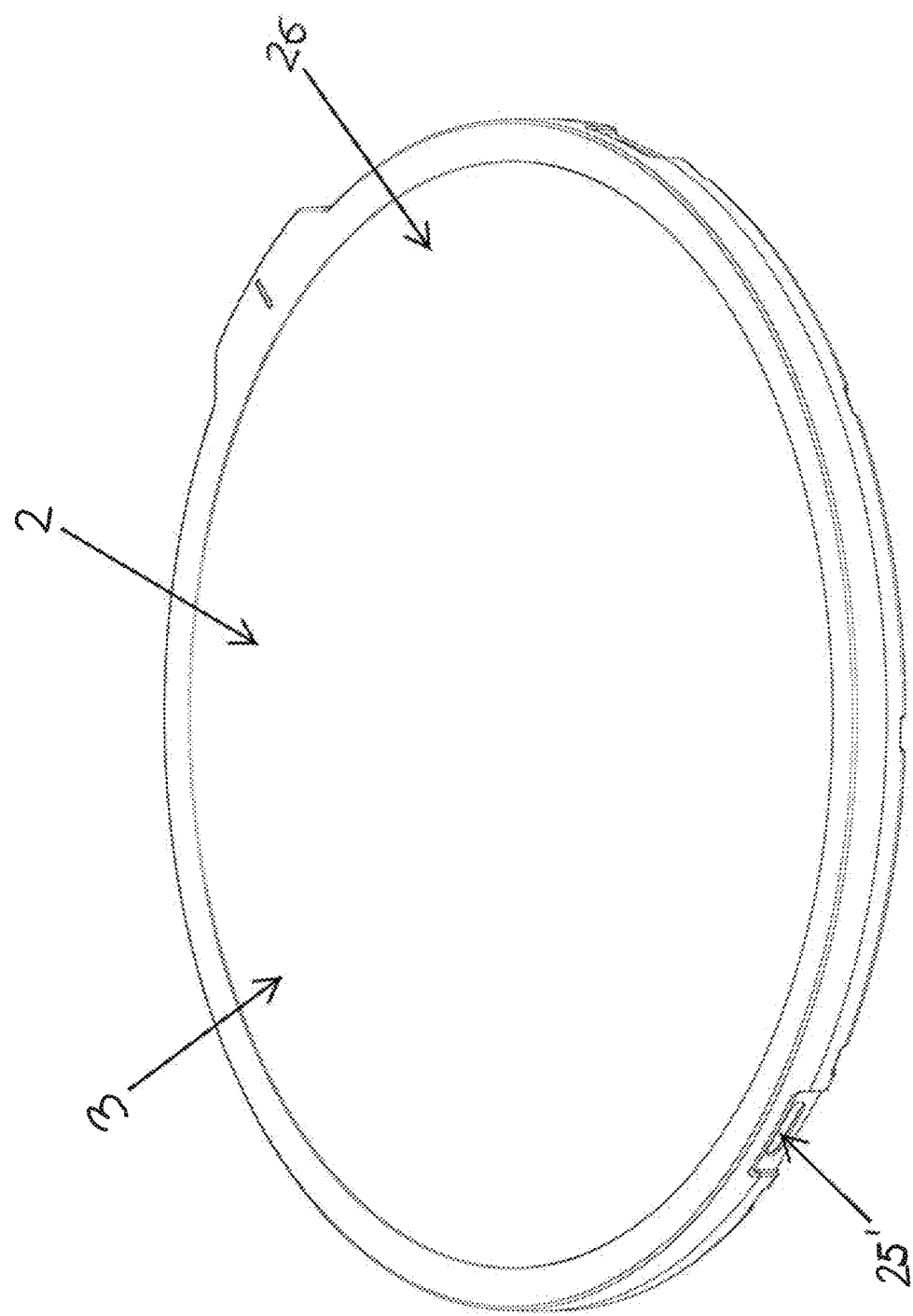
FIG. 2 shows a diagrammatic view of the measuring platform of the device illustrated in FIG. 1.

FIG. 1 shows a device 1 for posturography with which an analysis of a user's posture can be performed. The training equipment 1 comprises a measuring platform 2, which is illustrated in FIG. 2. A standing surface 3 is provided on the upper side of the measuring platform 2, on which standing surface 3 the person to be examined stands during posturography.

Figure 3:
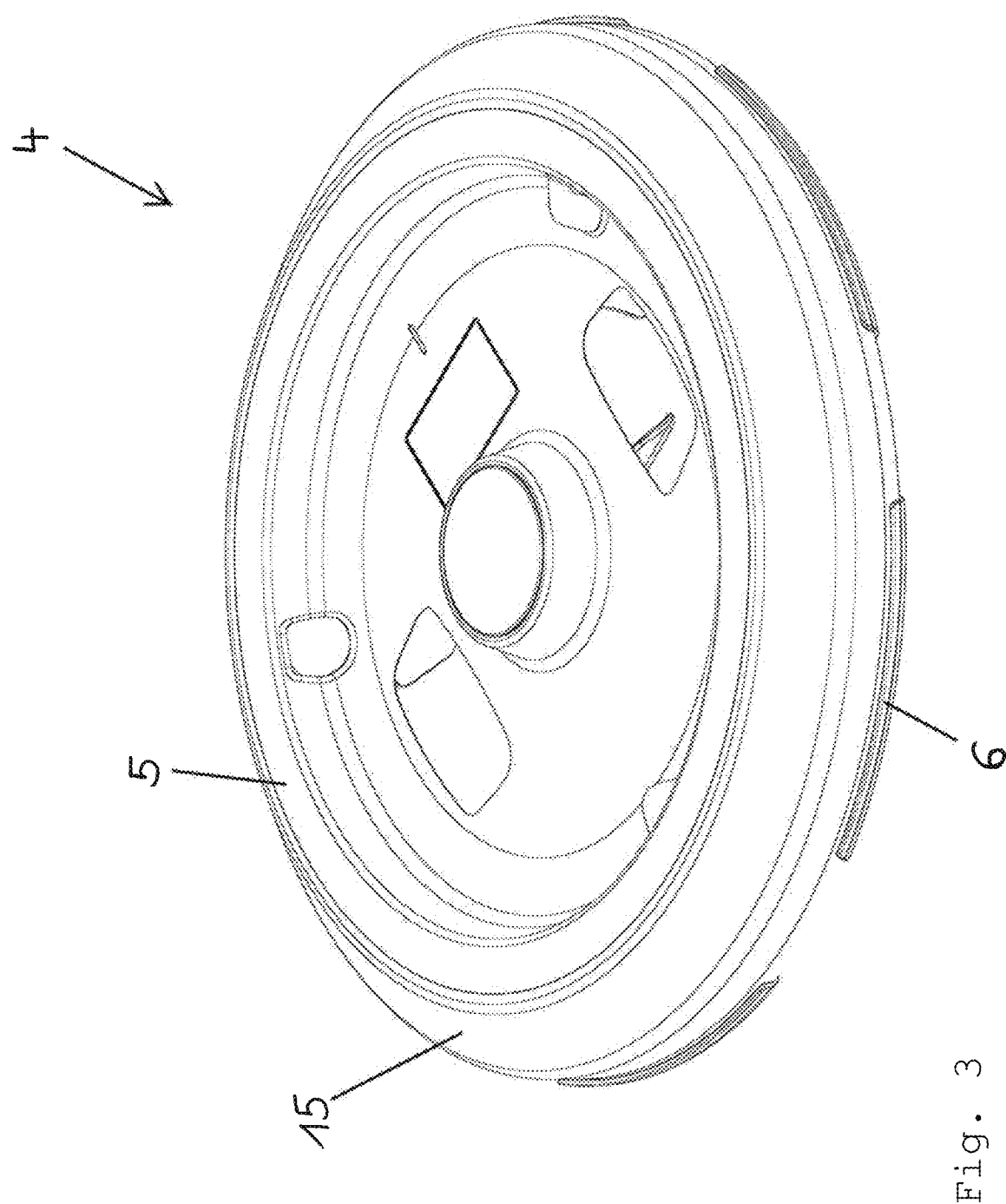
FIG. 3 shows a diagrammatic view of the damping member of the device illustrated in FIG. 1.

As further can be seen in FIG. 1, the training equipment 1 also comprises a damping member 4 (see FIG. 3) which comprises a tilting plate 5 on the upper side and a support plate 6 on the underside. The measuring platform 2, together with the tilting plate 5 of the damping member 4, is supported tiltably relative to the support plate 6 of the damping member 4 by means of a tilting apparatus 7. In the embodiment shown, the tilting apparatus 7 comprises a joint 8, a universal joint in the embodiment shown, between the tilting plate 5 and the support plate 6. The universal joint 8 is arranged along a central axis of the measuring platform 2. The measuring platform 2 can tilt in all directions about the central axis during posturography by means of the tilting joint 8.

As further can be seen from FIG. 1, the training equipment 1 additionally comprises a base element 9 (see FIG. 4) which is connected to an air cushion means 10 on the underside. An air cushion bearing the base element 9 can be formed during posturography with the aid of the air cushion means 10. The air cushion means 10 comprises an annular circumferential sealing member 10' in the form of a hose ring or annular body. The sealing member 10' delimits an overpressure chamber 11 below the base element 9, which chamber 11 is connected to an air pressure apparatus (not shown). Due to the air cushion, the measuring platform 2 can be moved substantially freely in all directions in the horizontal plane during posturography. In addition, the base element 9 is connected on the underside to a tubular guide member 12, which is movable within a receiving member 13. Thereby maximum horizontal mobility of the measuring platform 2 can be limited. The receiving member 13 comprises a damping stop 13' on the inner side, made of an elastically deformable damping material, for example foam material. A hard stop of the guide member 12 can thus be avoided, which would impair the informative value of the collected movement data. In the embodiment shown the damping stop 13' is formed annularly. In addition, in FIG. 1 can be seen a restoring member 13" in the form of an elastic cable, by which the guide member 12 is reset in the direction of a center position within the receiving member 13. The elastic cables have the task of centering the entire inner part so that the same initial image is always ensured during the measurement.

Figure 4:
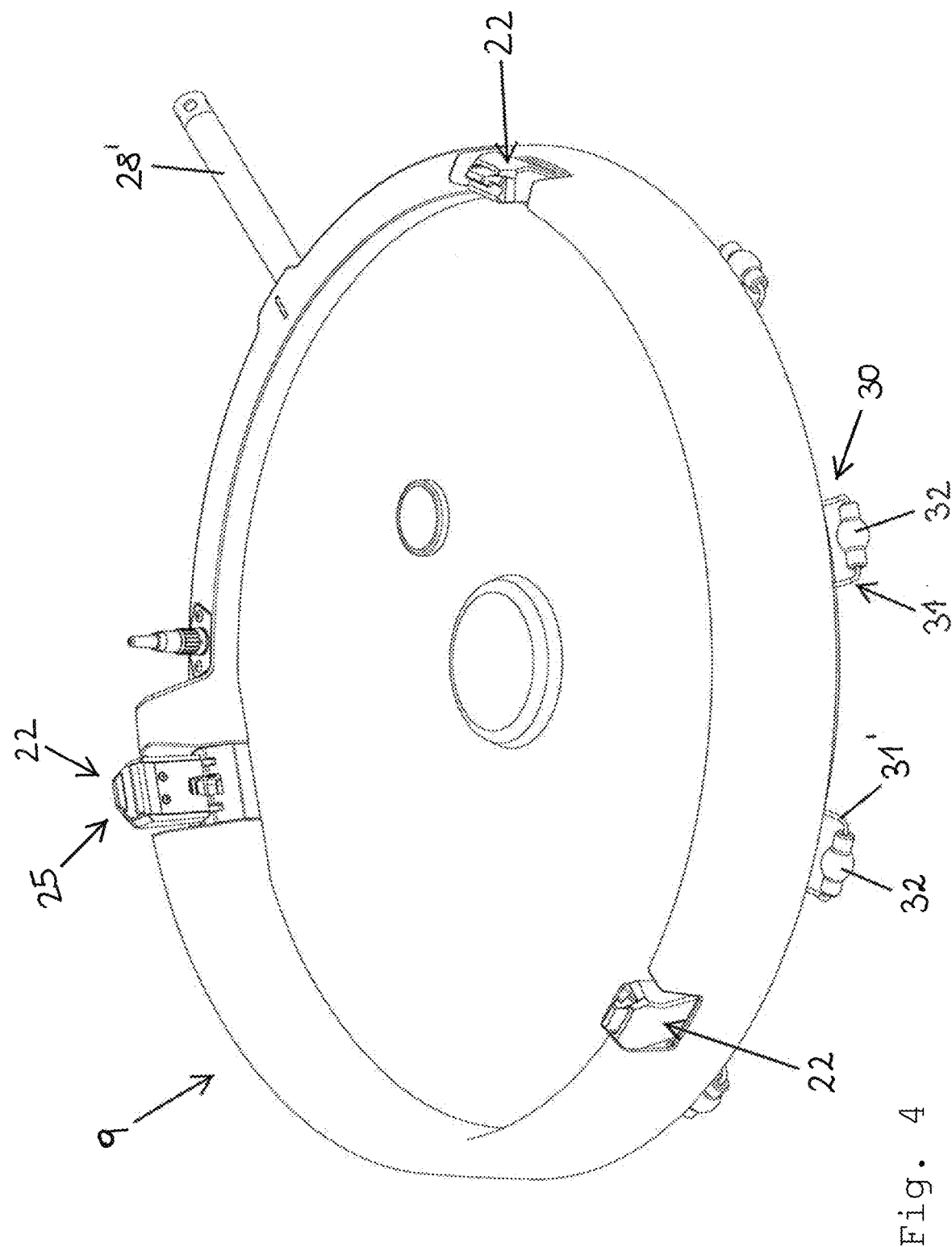
FIG. 4 shows a diagrammatic view of the base element of the device illustrated in FIG. 1.

As can further be seen in FIG. 1, the spring and damping member 4 comprises a damping material 15 between the measuring platform 2 and the base element 9, by which damping material 15 any tilting motions of the measuring platform 2 are damped. Due to the damping material 15, a pivoting of the measuring platform 2 with respect to its main longitudinal plane is therefore braked gently. In the embodiment shown, the damping material 15 extends annularly circumferentially below the measuring platform 2. In FIG. 4, the measuring platform 2 is shown in a substantially horizontal center position, from which the measuring platform 2 can be tilted in all directions during posturography. In the center position shown, the damping material 15 is disposed against the underside of the tilting plate 5 or of the measuring platform 2 so that the damping effect occurs immediately when tipping from the center position. For purposes of this disclosure, the directional indications, such as "up", "down", etc. refer to the shown operating position of the device 1.

As can further be seen from FIG. 1, the damping material 15 in the embodiment shown is formed tapered in the cross-section in the direction of the measuring platform 2, i.e., toward the top. Various cross-sectional geometries of the damping material 15 may be provided for adapting the damping characteristic.

In the embodiment shown, an open-cell foam material is provided as damping material 15, with which the desired damping is achieved, but at the same time the maximum tilt angle required for posturography of approximately 10 degrees with respect to the horizontal resting position is ensured. During posturography, the measuring platform can permanently tip up to 10 degrees in all directions, wherein the test person is always kept in motion by the damping.

As can be seen in FIG. 1, the device 1 for posturography comprises a modular construction, wherein on the one hand the damping member 4 is connected to the base element 9 via a connection 16 which is releasable without a tool and, on the other hand, the measuring platform 2 is connected to the damping member 4 via a further connection 17 which is releasable without a tool. In the embodiment shown, the damping member 4 can be placed on the base element 9 in the intended position. For this purpose, the base element 9 comprises a central elevation 18 into which a corresponding depression 19 of the damping member 4 fits. In addition, the damping member 4 comprises a centering recess 20 for receiving a corresponding centering member 21 of the base element 9.

As can further be seen in FIG. 1, at least three rocker arm members 22 are provided between the base element 9 and the measuring platform 2, which are pivotable in the direction of arrow 23 between a release position (not shown) which releases the tilting movement of the measuring platform and a blocking position (see FIG. 1) which blocks the tilting movement of the measuring platform 2. In the embodiment shown the rocker arm members 22 are pivotally supported via joints 24 on the base element 9. Latching members 25 in the form of latching lugs are respectively provided on the rocker arm members 22, with which latching members 25 the rocker arm members 22 are latchable in the blocking position with corresponding latching means 25' on the measuring platform 2 (see FIG. 2).

As can further be seen in FIG. 1, the measuring platform 2 comprises a circular sensor film 26 for the formation of the standing surface 3, which sensor film 26 is formed with a plurality of pressure sensors. The sensor film 26 is arranged below a covering film, by which the sensor film 26 is protected against shear forces. The pressure sensors are regularly distributed across the standing surface 3 in order to accurately measure the equilibrium displacement of the test person. In the embodiment shown, the sensor film 26 is composed of four substantially quarter circle sensor film parts. The pressure sensors of the individual sensor film parts are each connected to a signal pick-up 27 which is connected to a computing apparatus (not shown) via data transfer lines 28 and 28' (see FIG. 4).

As can further be seen in FIG. 1, the base element 9 is movably arranged in a schematically shown frame element 29 with the receiving member 13 in the horizontal plane. Spacer members 30 are provided between the base element 9 and the frame element 29 (see also FIG. 4). The spacer members 30 each comprise a spring member 31 which is elastically deformable in the vertical direction and is formed by two bow springs 31' in the embodiment shown. The spacer members 30 each comprise, on the side of the frame element 20, a spherical sliding member 32 for sliding on a sliding surface 33 of the frame element 29.

Figure 5:
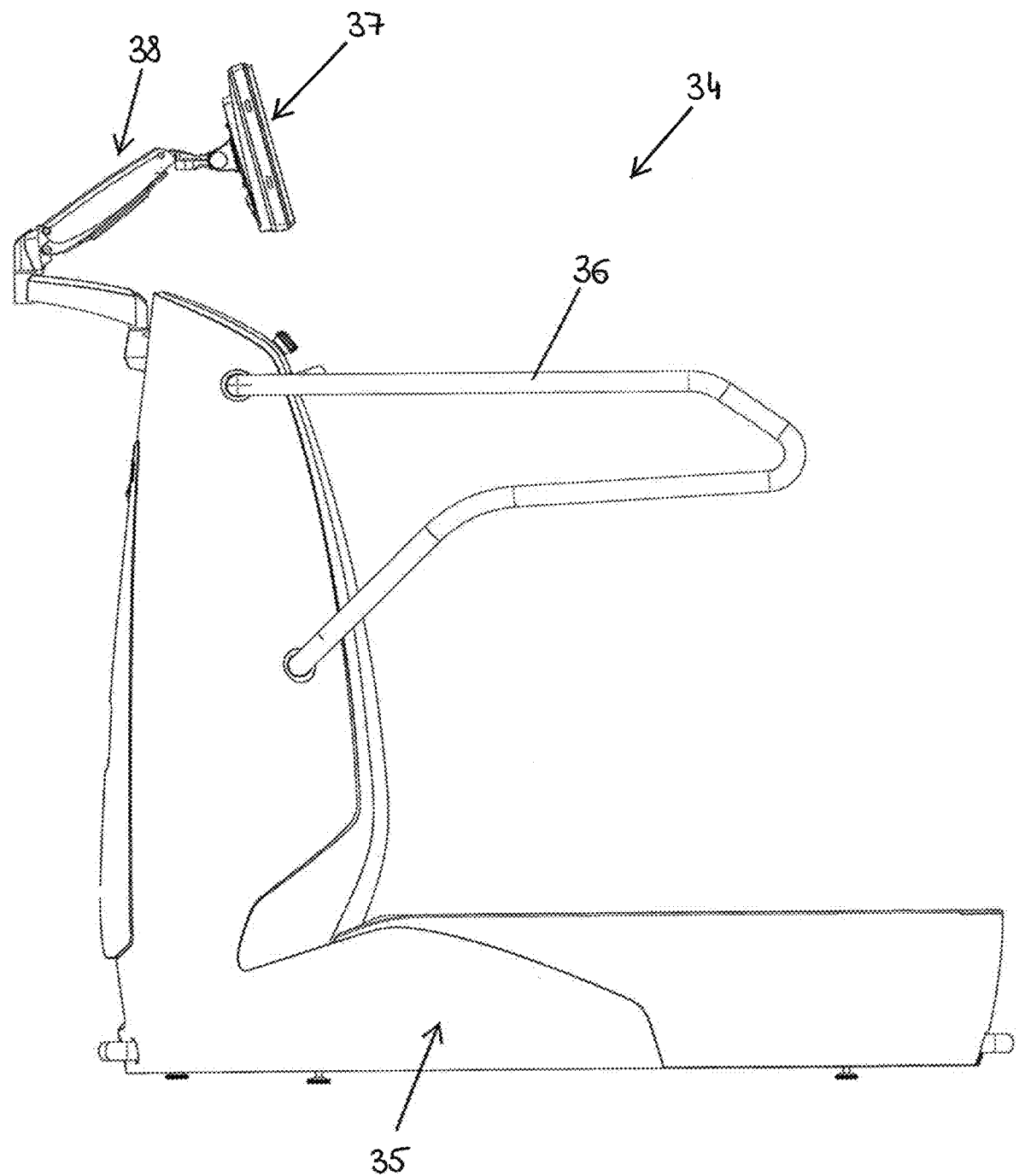
FIG. 5 shows a side view.
Figure 6:
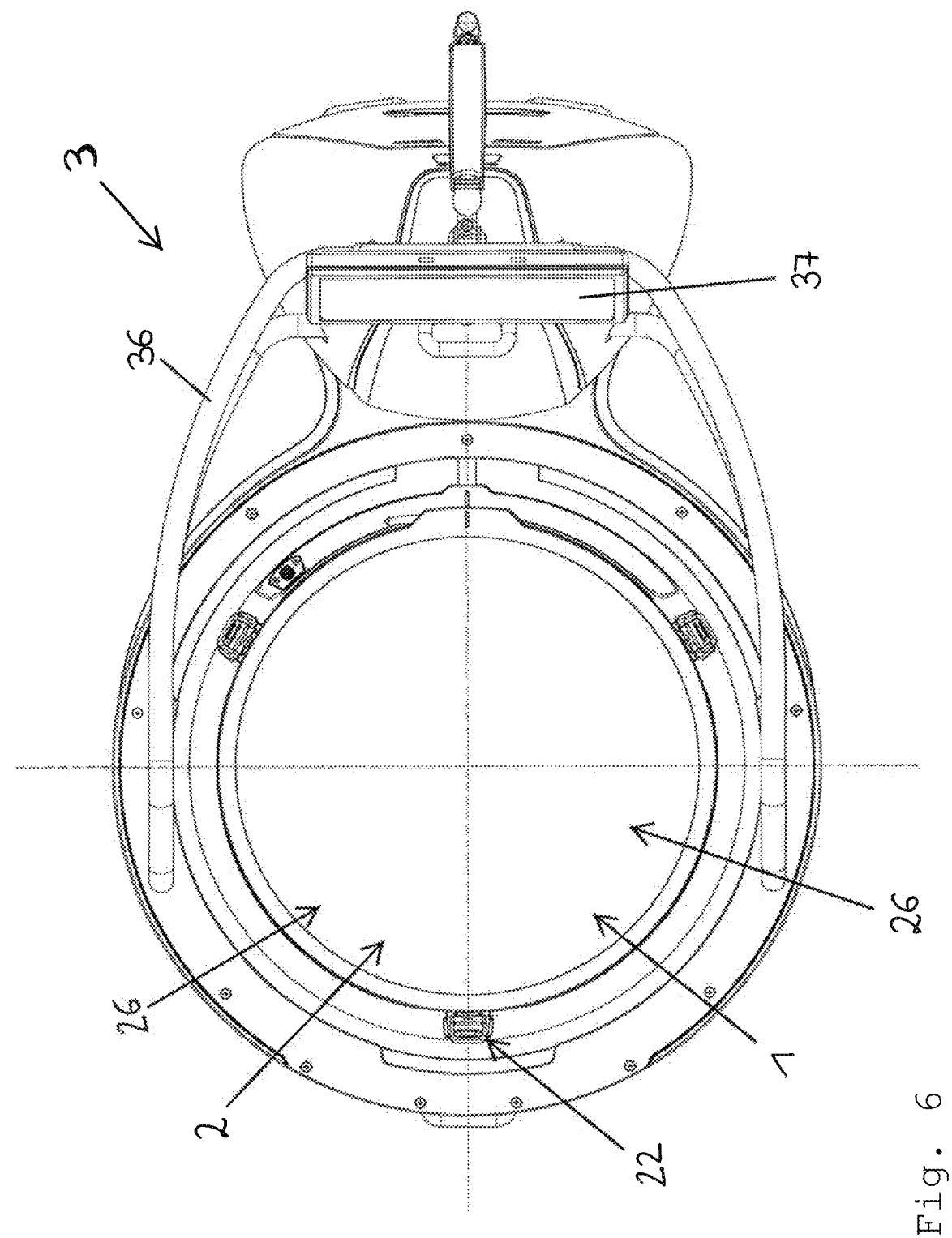
FIG. 6 shows a plan view.
Figure 7:
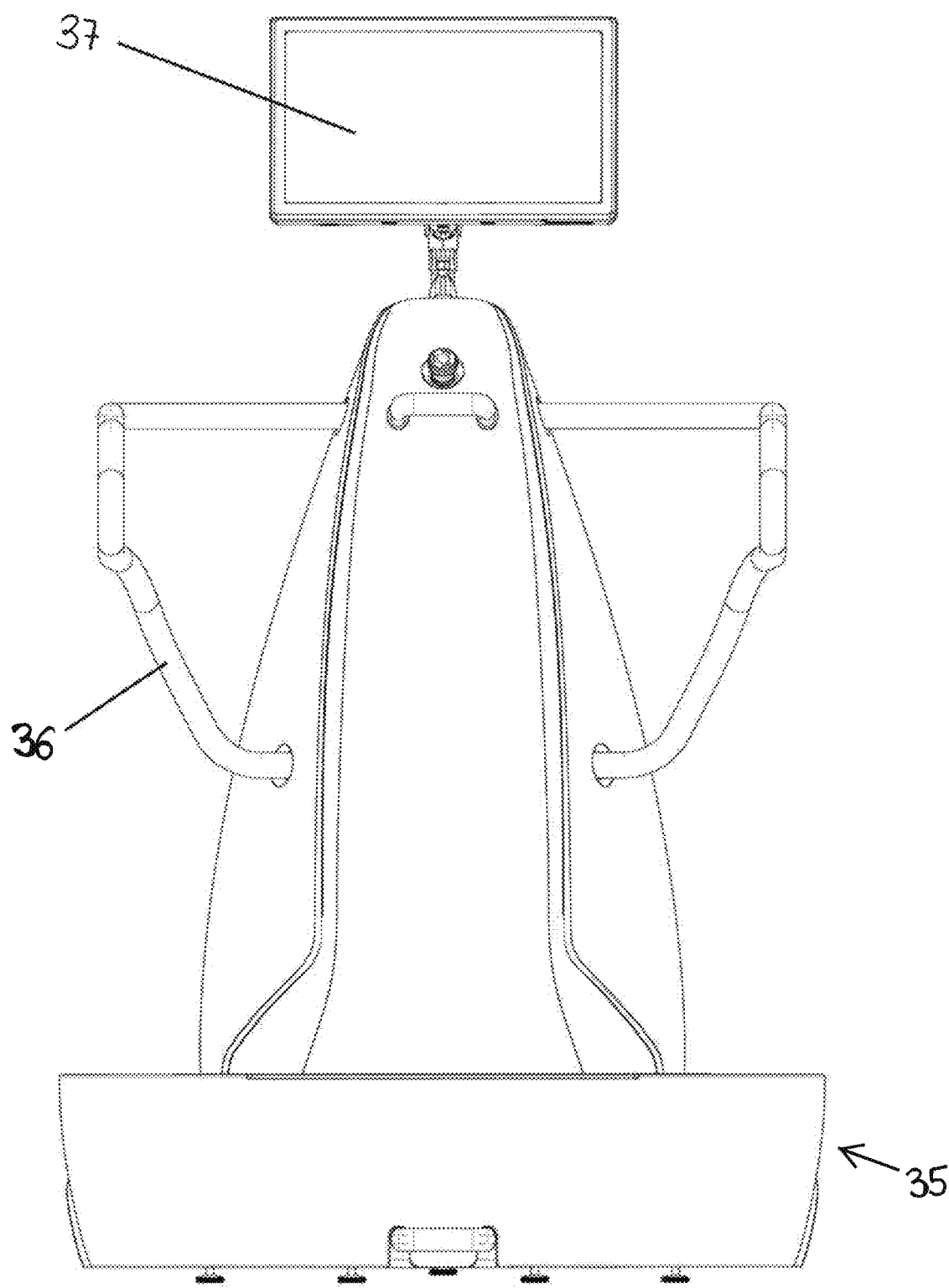
FIG. 7 shows a front view of a diagnostic and therapeutic tool in which the device according to FIGS. 1 to 4 is employed.

FIGS. 5 to 7 show a diagnostic and therapeutic tool 34, in which the device 1 according to FIGS. 1 to 4 is used. The diagnostic and therapeutic tool 34 comprises a frame structure 35 with the frame element 29 in which the receiving member 13 for the inner part comprised of the measuring platform 2, the damping member 4 and the base element 9 is formed. Furthermore, a handrail 36 on which the test person can hold can be seen. In addition, a screen 37 for displaying information is shown, which is pivotally supported on a retaining arm 38.

FIG. 8 shows an alternative embodiment of the device 1 for posturography, wherein in the following only the differences from the preceding embodiment are to be considered.

According to FIG. 8, the damping material 15 comprises a substantially parabolic boundary surface 15a in the cross-section (i.e., in an intersecting plane perpendicular to the main plane of the measuring platform in the center position). Accordingly, the outer side of the damping member 4, on which the measuring platform 2 rests, is curved parabolically. Moreover, in the embodiment shown, the damping material 15 comprises a first layer 15b on the side of the measuring platform 2 and a second layer 15c on the side of the base element 9. The second layer 15c is harder than the first layer 15b so that the second layer 15c has a larger deformation resistance than the first layer 15b. Both measures have the effect that the damping behavior of the damping member 4 is progressive with respect to the tilt angle. Thereby the destabilization of the test person decreases with the tilt angle.

The invention claimed is:

1. A device for posturography having a measuring platform, which comprises a standing surface for a test person, having a base element on which the measuring platform is tiltably supported by means of a tilting apparatus including a joint, and having an air cushion device supporting the base element and positioned below the base element, wherein a damping member having a damping material is arranged between the measuring platform and the base element, by which damping member a tilting movement of the measuring platform is damped, wherein the damping material has a shape of a ring and is tapered from a lower side facing away from the measuring platform towards an upper side facing the measuring platform, and wherein the tapered upper side of the damping material does not project beyond an underside of the measuring platform in a radial direction of the measuring platform.

2. The device for posturography according to claim 1, wherein the damping material is arranged circumferentially between the measuring platform and the base element.

3. The device for posturography according to claim 2, wherein, in a horizontal position of the measuring platform, the underside of the measuring platform rests against the damping material.

4. The device for posturography according to claim 1, wherein the damping material is tapered in a cross-section in a direction of the measuring platform.

5. The device for posturography according to claim 4, wherein the damping material comprises a parabolic boundary surface in the cross-section.

6. The device for posturography according to claim 1, wherein the damping material comprises a first layer on a side of the measuring platform and a second layer on a side of the base element, wherein the second layer is harder than the first layer.

7. The device for posturography according to claim 1, wherein a foam material is provided as the damping material.

8. The device for posturography according to claim 1, wherein the damping member is connected to the base element via a releasable connection and/or that the measuring platform is connected to the damping member via another releasable connection.

9. The device for posturography according to claim 1, wherein the damping member comprises at least one centering opening for receiving a corresponding centering member of the base element.

10. The device for posturography according to claim 1, wherein at least three rocker arm members are provided between the base element or the damping member and the measuring platform, which rocker arm members are pivotable between a releasing position which releases the tilting movement of the measuring platform and a blocking position which blocks the tilting movement of the measuring platform.

11. The device for posturography according to claim 10, wherein latches are provided on the rocker arm members for latching in the blocking position.

12. The device for posturography according to claim 1, wherein the measuring platform comprises a plurality of pressure sensors, which is arranged substantially regularly on the standing surface.

13. The device for posturography according to claim 12, wherein the measuring platform comprises a circular sensor film having the pressure sensors for formation of the standing surface, which sensor film is composed of multiple sensor film parts.

14. The device for posturography according to claim 12, wherein the pressure sensors of the sensor film parts are connected to signal pick-ups which are connected to a computing apparatus via data transfer lines.

15. The device for posturography according to claim 1, wherein the air cushion device comprises a circumferential sealing member delimiting an overpressure chamber.

16. The device for posturography according to claim 1, wherein the base element is arranged movably in a horizontal plane in a frame element.

17. The device for posturography according to claim 16, wherein the frame element comprises a receiving member for a guide member of the base element, wherein a damping stop is formed between the guide member and the receiving member.

18. The device for posturography according to claim 16, wherein a spacer member is provided between the base element and the frame element.

19. The device for posturography according to claim 18, wherein the spacer member comprises a spring member which is elastically deformable in a vertical direction.

20. The device for posturography according to claim 18, wherein the spacer member comprises a sliding member for sliding on a sliding surface of a frame element.

21. A device for posturography having a measuring platform, the device for posturography comprising:
a standing surface for a test person, having a base element on which the measuring platform is tiltably supported by means of a tilting apparatus including a joint,
an air cushion device supporting the base element and positioned below the base element,
a damping member having a damping material is arranged between the measuring platform and the base element, by which damping member a tilting movement of the measuring platform is damped, and the damping material has a shape of a ring and is tapered from a lower side facing away from the measuring platform towards an upper side facing the measuring platform, and the tapered upper side of the damping material does not project beyond an underside of the measuring platform in a radial direction of the measuring platform, and the taper of the damping material produces a damping effect at a first deflection which is less than a damping effect at a second, greater deflection.

* * * * *